United States Patent
Itakura et al.

(10) Patent No.: US 7,673,493 B2
(45) Date of Patent: Mar. 9, 2010

(54) INSPECTION DEVICE FOR HUMIDITY SENSOR AND METHOD FOR ADJUSTING SENSOR CHARACTERISTICS OF HUMIDITY SENSOR

(75) Inventors: Toshikazu Itakura, Toyota (JP); Toshiki Isogai, Nagoya (JP)

(73) Assignees: DENSO CORPORATION, Kariya (JP); Nippon Soken, Inc., Nishio (JP)

( * ) Notice: Subject to any disclaimer, the term of this patent is extended or adjusted under 35 U.S.C. 154(b) by 459 days.

(21) Appl. No.: 11/727,994

(22) Filed: Mar. 29, 2007

(65) Prior Publication Data

US 2007/0169535 A1 Jul. 26, 2007

Related U.S. Application Data

(62) Division of application No. 11/362,822, filed on Feb. 28, 2006, now Pat. No. 7,213,441.

(30) Foreign Application Priority Data

Mar. 8, 2005 (JP) ............................... 2005-64405

(51) Int. Cl.
*G01N 21/00* (2006.01)
(52) U.S. Cl. ...................................... 73/1.06
(58) Field of Classification Search ............... None
See application file for complete search history.

(56) References Cited

U.S. PATENT DOCUMENTS

| | | | |
|---|---|---|---|
| 4,017,820 A | 4/1977 | Ross | |
| 4,642,601 A | 2/1987 | Sugawara et al. | |
| 4,793,182 A | 12/1988 | Djorup | |
| 4,825,684 A | 5/1989 | Nishiguchi et al. | |
| 6,037,793 A | 3/2000 | Miyazawa | |
| 7,058,518 B2 | 6/2006 | Shoji | |
| 2006/0053862 A1* | 3/2006 | Mayer et al. | .............. 73/1.06 |

FOREIGN PATENT DOCUMENTS

| | | |
|---|---|---|
| JP | A-S52-035690 | 3/1977 |
| JP | A-53-144682 | 12/1978 |
| JP | A-5-160210 | 6/1993 |
| JP | A-6-349909 | 12/1994 |
| JP | A-9-298225 | 11/1997 |
| JP | A-2003-28824 | 1/2003 |

OTHER PUBLICATIONS

Office Action dated Feb. 12, 2008 in corresponding German Patent Application No. 10 2006 010 777.2-52 (and English translation).
Office Action dated Aug. 3, 2008 in corresponding Chinese Patent Application No. 200610059805.9 (and English translation).

* cited by examiner

*Primary Examiner*—Robert R Raevis
(74) *Attorney, Agent, or Firm*—Posz Law Group, PLC

(57) ABSTRACT

An inspection device inspects a humidity sensor having a sensor portion and a circuit portion, which are integrated into one chip. The inspection device includes: an inspection chamber for accommodating a wafer, in which a plurality of humidity sensors are disposed as a sensor chip in a wafer state; a probe for contacting an electrode pad of the circuit portion; a tester electrically connected to the probe for inspecting electric properties of the humidity sensor; and a temperature-humidity control portion for controlling a temperature and a humidity in the inspection chamber.

7 Claims, 3 Drawing Sheets

INSPECTION DEVICE FOR HUMIDITY SENSOR AND METHOD FOR ADJUSTING SENSOR CHARACTERISTICS OF HUMIDITY SENSOR

CROSS REFERENCE TO RELATED APPLICATION

This application is a division of application Ser. No. 11/362,822 filed on Feb. 28, 2006, which is based on Japanese Patent Application No. 2005-64405 filed on Mar. 8, 2005, the disclosure of which is incorporated herein by reference.

FIELD OF THE INVENTION

The present invention relates to an inspection device for inspecting a humidity sensor in a wafer state and a method for adjusting the sensor characteristics of the humidity sensor in the wafer state.

BACKGROUND OF THE INVENTION

Conventionally, an inspection device for inspection sensor characteristics and electrical characteristics (electric properties) of an IC chip in the sensor is disclosed in, for example, U.S. Pat. No. 6,037,793. Here, the IC chip as a sensor chip is formed on a semiconductor wafer.

The inspection device includes an inspection chamber (i.e., a probe chamber) for accommodating a semiconductor wafer, a probe (i.e., a probe of a probe card) as a contact member for contacting an electrode pad of the IC chip, and a tester for inspecting the electrical characteristics of the IC chip. The device performs the inspection of the electrical characteristics as a probing test so that the quality of the IC chip is checked.

When the IC chip is a sensor, not only the probing test for inspecting the electrical characteristics of the sensor but also a sensor characteristic test for inspecting sensor characteristics of the sensor is performed. On the basis of the sensor characteristic test, the sensor characteristics are adjusted. In general, this sensor characteristic test and adjustment of the sensor characteristics are performed after the sensor is packaged. Preferably, the sensor characteristic test and the adjustment of the sensor characteristics are performed in an earlier step of a manufacturing process of the sensor. This is because time loss and/or cost of manufacturing the sensor are reduced when a defective product of the sensor is eliminated in the earlier step. The defective product is decided on the basis of the sensor characteristic test and the adjustment of the sensor characteristics.

Accordingly, it is considered that the sensor characteristic test and the adjustment of the sensor characteristics are performed on a wafer to be a sensor chip. Specifically, a sensor portion and a circuit portion for processing a signal from the sensor portion are integrated into one IC chip so that one IC chip provides the sensor. The wafer includes multiple IC chips, and the wafer is divided into multiple chips so that each sensor is provided. However, when the sensor is a humidity sensor, it is required to inspecting and adjusting the sensor characteristics at different multiple temperature-humidity conditions having different humidity and different temperature. Here, the sensor characteristics include, for example, sensitivity of the sensor, temperature dependency (i.e., temperature characteristic) of the sensitivity, offset of the sensor and temperature dependency (i.e., temperature characteristic) of the offset. Even when the sensor portion and the circuit portion in the sensor are integrated into one IC chip, the inspection device disclosed in U.S. Pat. No. 6,037,793 cannot inspect the sensor characteristics of the sensor, which is in a wafer state before the sensor is divided from the wafer.

SUMMARY OF THE INVENTION

In view of the above-described problem, it is an object of the present invention to provide an inspection device for inspecting a sensor in a wafer state. It is another object of the present invention to provide a method for adjusting sensor characteristics of the humidity sensor in the wafer state.

An inspection device inspects a humidity sensor having a sensor portion and a circuit portion, which are integrated into one chip. The sensor portion is capable of detecting humidity of atmosphere, and the circuit portion is electrically connected to the sensor portion so that the circuit portion is capable of processing a detection signal of the sensor portion. The inspection device includes: an inspection chamber for accommodating a wafer, the wafer in which a plurality of humidity sensors are disposed as a sensor chip in a wafer state; a probe as a contact member for contacting an electrode pad of the circuit portion, wherein the probe is disposed in the inspection chamber; a tester for inspecting electric properties of the humidity sensor in the wafer state, wherein the tester is electrically connected to the probe for inspecting the humidity sensor; and a temperature-humidity control portion for controlling a temperature and a humidity in the inspection chamber.

In the above inspection device, since the temperature-humidity control portion controls a temperature and a humidity in the inspection chamber to be a predetermined temperature-humidity condition, not only the probing test but also the sensor characteristic test are performed by the tester. Thus, the manufacturing cost of the humidity sensor is reduced. Further, by performing the sensor characteristic test and the probing test simultaneously, the manufacturing cost of the humidity sensor is much reduced.

Further, an inspection device inspects a humidity sensor having a sensor portion and a circuit portion, which are integrated into one chip. The sensor portion is capable of detecting humidity of atmosphere, and the circuit portion is electrically connected to the sensor portion so that the circuit portion is capable of processing a detection signal of the sensor portion. The inspection device includes: a plurality of inspection chambers for accommodating a wafer, the wafer in which a plurality of humidity sensors are disposed as a sensor chip in a wafer state; a probe as a contact member for contacting an electrode pad of the circuit portion, wherein the probe is disposed in the inspection chamber; and a tester for inspecting electric properties of the humidity sensor in the wafer state, wherein the tester is electrically connected to the probe for inspecting the humidity sensor. Each inspection chamber has a different temperature and a different humidity, and the wafer is transported from one inspection chamber to another in turn so that the tester inspects the humidity sensor in the wafer state under different temperature-humidity conditions.

In the above inspection device, the wafer is transported from one inspection chamber to another. Thus, the sensor characteristics of the humidity sensor are inspected effectively. Thus, the manufacturing cost of the humidity sensor is reduced. Further, since each inspection chamber is preliminarily controlled to have a predetermined temperature and a predetermined humidity, the waiting time for starting the test is shortened. Accordingly, many humidity sensors can be inspected within short time.

Further, a method for adjusting sensor characteristics of a humidity sensor is provided. The humidity sensor has a sensor portion and a circuit portion, which are integrated into one chip. The sensor portion is capable of detecting humidity of atmosphere, and the circuit portion is electrically connected to the sensor portion so that the circuit portion is capable of processing a detection signal of the sensor portion. The method includes the steps of: controlling a temperature and a humidity around a wafer to be a predetermined temperature-humidity condition, the wafer in which a plurality of humidity sensors are disposed as a sensor chip in a wafer state before the wafer is divided into a plurality of sensor chips; measuring electric properties of the humidity sensor under the predetermined temperature-humidity condition; and adjusting a sensitivity, a temperature characteristic of the sensitivity, an offset and a temperature characteristic of the offset in the humidity sensor on the basis of a measurement result of the electric properties of the humidity sensor.

In the above method, not only the probing test but also the sensor characteristic test are performed even when the humidity sensor is in the wafer state, i.e., even when the wafer is not divided into multiple sensor chip. Further, on the basis of the test result, the sensor characteristics of the humidity sensor are adjusted. Thus, the manufacturing cost of the humidity sensor is reduced.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

First Embodiment

Figure 1A:
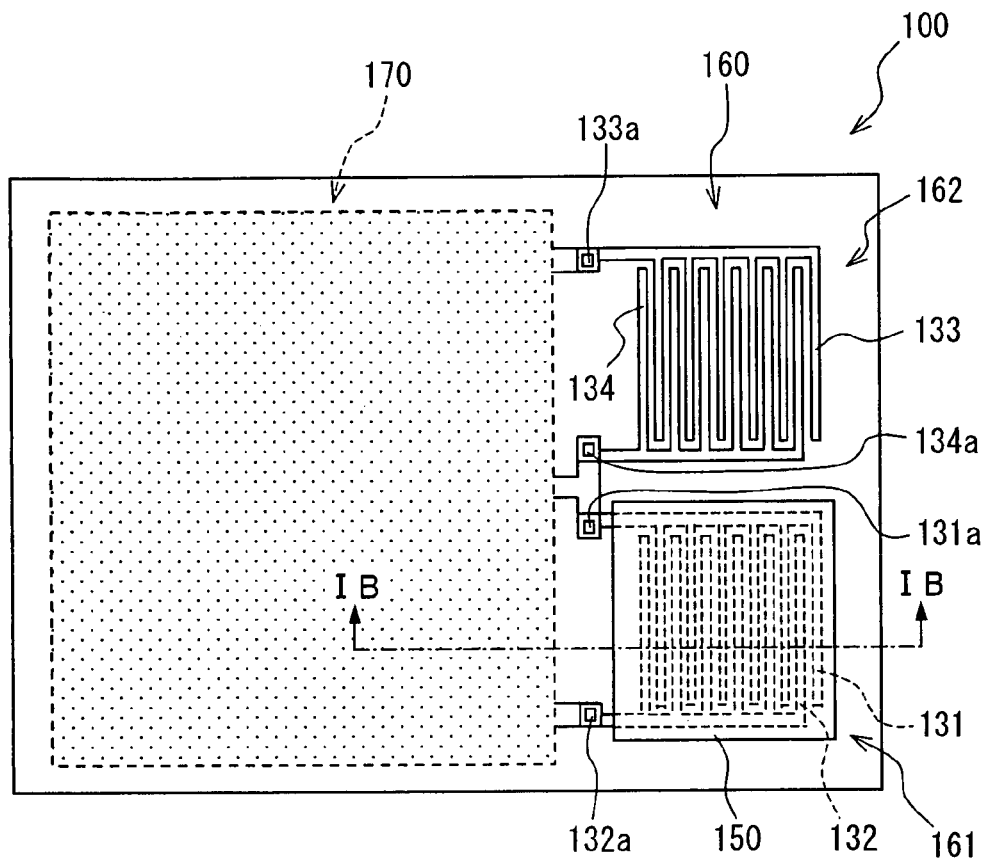
FIG. 1A is a schematic plan view showing a humidity sensor as an object of inspection, according to a first embodiment of the present invention.
Figure 1B:
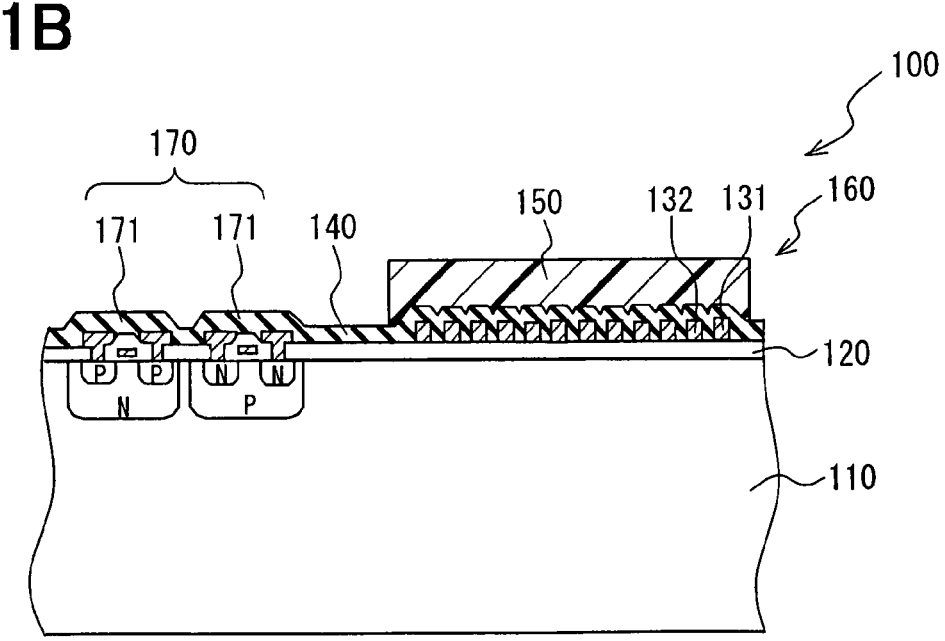
FIG. 1B is a partial cross sectional view showing the sensor taken along line IB-IB in FIG. 1A.
Figure 2:
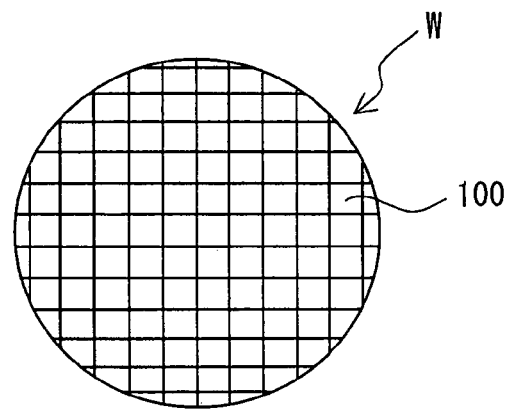
FIG. 2 is a plan view showing a wafer, in which multiple humidity sensors are disposed.

A humidity sensor 100 as an object of inspection of an inspection device according to a first embodiment of the present invention is shown in FIGS. 1A and 1B. The sensor 100 is formed to be one chip in a semiconductor wafer. In FIG. 1A, a circuit portion is omitted to show, and an electrode and a wiring are partially illustrated transparently.

It is required to decide whether an IC chip is a defective product and to select the IC chip as a non-defective product on the basis of a probing test as an electrical characteristic test before the wafer is divided into multiple IC chips. Specifically, the IC chip as a sensor chip in the wafer state is inspected by the inspection device whether electric parts such as a transistor and a resistor for composing the IC chip are normally formed without defect and whether the electric parts normally function as an electric circuit of the non-defective product.

When the IC chip is a sensor, it is required to perform a sensor characteristic test for detecting sensor characteristics of the sensor. On the basis of the sensor characteristic test result, it is required to adjust the sensor characteristics of the sensor. Here, the sensor having the sensor characteristics, which are in an adjustable range, is to be adjusted. The sensor having the sensor characteristics, which are out of the adjustable range or are impossible to adjust, is selected as a sensor characteristic failure, i.e., a defective product. Accordingly, it is preferred that the adjustment and the sensor characteristic test are performed in an earlier step of the manufacturing process of the sensor. When a defective product of the sensor is eliminated in the earlier step, time loss and/or manufacturing cost of the sensor are reduced.

However, in a conventional humidity sensor having a sensor portion and a circuit portion, which are individually formed, a sensor characteristic test is performed after a wafer having multiple sensor portions is divided into multiple sensor chips and each sensor chip is mounted on a circuit board having the circuit portion. On the other hand, in this embodiment, in view of the above difficulty, the humidity sensor 100 is formed as follows.

As shown in FIG. 1B, the sensor 100 includes a semiconductor substrate 110, which is made of, for example, silicon. A silicon oxide film 120 as an insulation film is formed on a top surface of the substrate 110. A pair of detection electrodes 131, 132 is disposed on the silicon oxide film 120. The electrodes 131, 132 are separated each other, and disposed on the same plane of the silicon oxide film 120. Further, each electrode 131, 132 faces each other.

The shape of each electrode 131, 132 is a comb-shape. However, the shape of the electrode 131, 132 may be a different shape.

The detection electrode 131, 132 is made from wiring material such as aluminum, copper, gold, platinum and poly silicon. Specifically, the wiring material is deposited on the semiconductor substrate 110 by a vapor deposition method, a sputtering method or the like. Then, the wiring material film is patterned to be the comb-shape pattern by a photo-lithography method. The detection electrode 131, 132 is made of aluminum in this embodiment.

A pair of reference electrodes 133, 134 is formed on the silicon oxide film 120. Each reference electrode 133, 134 is separated each other and disposed on the same plane of the silicon oxide film 120. Further, each reference electrode 133, 134 faces each other. The reference electrode 133, 134 has the same pattern as the detection electrode 131, 132, and is made of the same material as the detection electrode 131, 132.

A silicon nitride film 140 as a protection film is formed on the substrate 110 to cover the detection electrodes 131, 132 and the reference electrodes 133, 134. The silicon nitride film 140 is deposited on the substrate 110 by a plasma CVD method or the like. The silicon nitride film 140 has a uniform thickness on each part of the substrate 110. When the detection electrode 131, 132 and the reference electrode 133, 134 have sufficient corrosion resistance against water, no protection film, i.e., the silicon nitride film 140 is necessitated. In FIG. 1A, the silicon nitride film 140 is not shown.

A humidity sensitive film 150 having hygroscopic property is formed on the silicon nitride film 140 to cover the detection electrodes 131, 132 and a clearance between the detection electrodes 131, 132. The humidity sensitive film 150 is made of, for example, poly-imide polymer. The humidity sensitive film 150 is formed in such a manner that the poly-imide polymer is applied on the substrate 110 by a spin coating method or a printing method and then the poly-imide polymer is heated and hardened. The humidity sensitive film 150 has temperature dependency of absorption/release of moisture, i.e., the absorption/release characteristic of moisture depends on temperature, so that the sensor output also depends on the temperature. Specifically, the sensor sensitivity and the offset of the sensor depend on the temperature.

In the humidity sensor 100, when the moisture, i.e., a water molecule penetrates into the humidity sensitive film 150, the relative permittivity of the humidity sensitive film 150 is changed in accordance with the moisture amount penetrated into the film 150. This is because the moisture, i.e., the water molecule has large relative permittivity. Thus, an electric capacitance of a capacitor formed between the detection electrodes 131, 132 is changed. The capacitor includes the humidity sensitive film 150 as a part of dielectric member. On the other hand, the reference electrodes 133, 134 have no humidity sensitive film 150. Therefore, the electric capacitance of the capacitor formed between the reference electrodes 133, 134 is not substantially changed or is changed a little. The moisture amount in the humidity sensitive film 150 corresponds to the humidity around the sensor 100. Thus, the humidity is detected on the basis of difference between the capacitance of the detection electrodes 31, 132 and the capacitance of the reference electrodes 133, 134. Here, the detection electrodes 131, 132 and the humidity sensitive film 150 provide a detection portion 161, and the reference electrodes 133, 134 provide a reference portion 162. The detection portion 161 and the reference portion 162 provide a sensor portion 160.

As shown in FIG. 1A, the detection electrodes 131, 132 and the reference electrodes 133, 134 have electrode pads 131a, 132a, 133a, 134a as a connection terminal for an external circuit, respectively. Each pad 131a, 132a, 133a, 134a is formed on an end of the electrode 131, 132, 133, 134. The detection electrodes 131, 132 and the reference electrodes 133, 134 are connected to a circuit portion 170 having a C-V converter circuit (not shown) through the electrode pads 131a, 132a, 133a, 134a. As shown in FIG. 1B, the circuit portion 170 includes a CMOS transistor 171 and the like. The capacitance change in the sensor portion 160 is processed in the circuit portion 170. A detection circuit in the circuit portion is disclosed in Japanese Patent Application Publication No. 2003-28824, the applicant of which is the same as the present application.

The humidity sensor 100 having the sensor portion 160 and the circuit portion 170 is formed as a IC chip in a wafer W. The wafer W has multiple IC chips for providing humidity sensors 100. Thus, the sensor portion 160 and the circuit portion 170 are formed on the substrate 110. The humidity sensor 100 in the wafer W can be tested and adjusted without dividing into each chip. Here, the humidity sensor 100 is minimized. Further, the humidity sensor can be made from conventional material so that the sensor 100 is formed by using a conventional semiconductor manufacturing line. Thus, the manufacturing cost of the sensor 100 becomes low.

Figure 3:
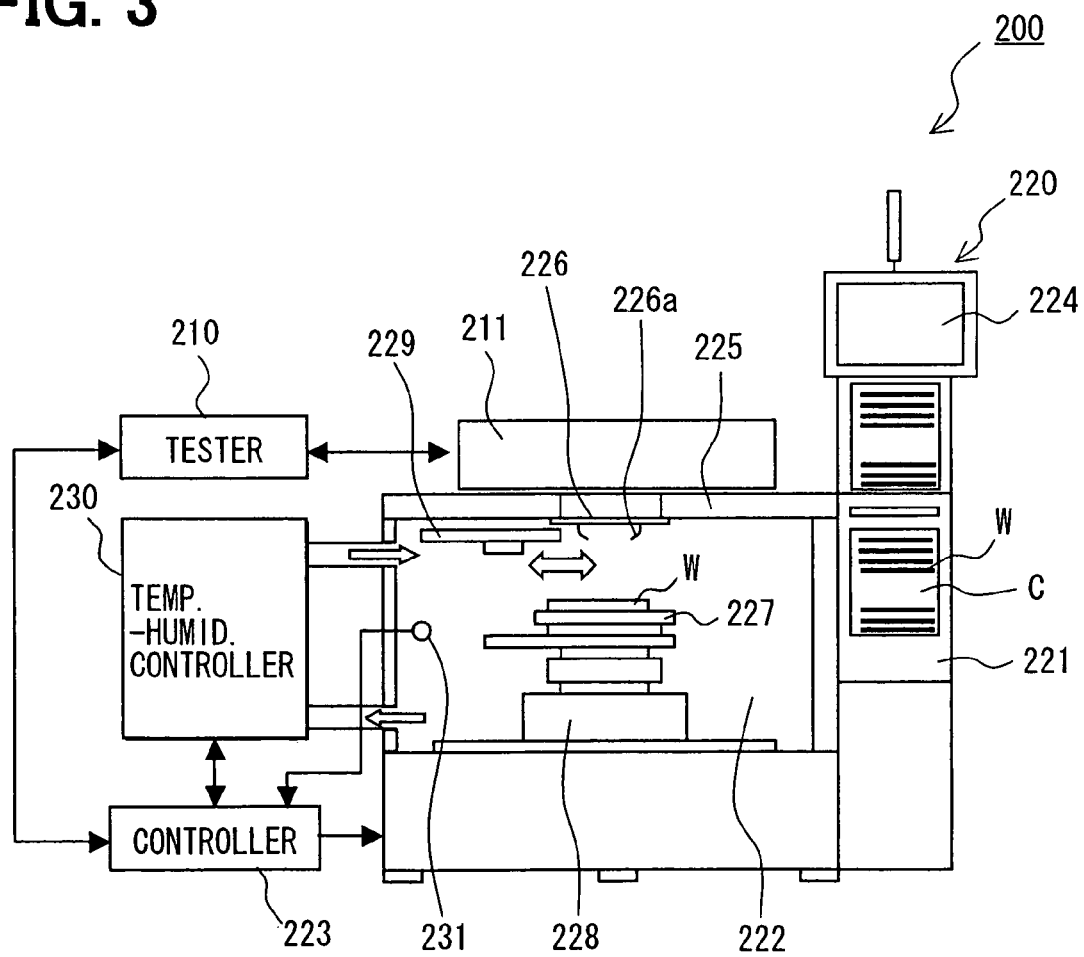
FIG. 3 is a schematic view showing an inspection device according to the first embodiment.

The sensor characteristics of the humidity sensor 100 in a state of the wafer W, i.e., the humidity sensor 100 without dividing into chips, are inspected by an inspection device 200. The inspection device 200 is shown in FIG. 3. The inspection device 200 includes a tester 210 and a probe device 220.

The probe device 220 includes a loader portion 221, a probe portion 222, a control portion 223 and a display portion 224. The loader portion 221 transports the wafer W accommodated in a cassette C. The probe portion 222 measures electric properties of the wafer W, which is transported from the loader portion 221. The control portion 223 controls the loader portion 221 and the probe portion 222 independently. The display portion 224 functions as an operation panel for operating the control portion 223, and displays information. The probe portion 222 provides a detection chamber, i.e., an inspection chamber.

The tester 210 includes a computer therein. The tester 210 performs a probing test for checking and selecting the IC in the sensor 100 and a sensor characteristic test of the humidity sensor 100 in the wafer W. Further, the tester 210 performs adjustment of the sensor characteristics on the basis of the result of the sensor characteristic test. Specifically, the tester 210 includes a tester head 211 disposed on the tester 210. The tester head 211 is connected to a probe card 226 electrically when the tester 210 performs the test. The probe card 226 is mounted on a head plate 225 of the probe portion 222. When the tester 210 is maintained or the like, the tester head 211 is detached from the probe portion 222. Thus, a signal can be communicated between the tester 210 and the humidity sensor 100 in the wafer W through the tester head 211 and the probe card 226.

A sub chuck (not shown) for preliminarily aligning the wafer W on the basis of a notch of the wafer is disposed in the loader portion 221. While the wafer W is transported from the loader portion 221 to the probe portion 222, the wafer W is preliminarily aligned by the sub chuck in the loader portion 221.

The probe portion 222 includes a main chuck 227, a driving element 228 and an alignment element 229. The main chuck 227 absorbs by vacuum and mounts the wafer W. The driving element 228 displaces the main chuck 227 in a X-, a Y-, a Z-, and a θ-direction. The alignment element 229 aligns the position of the wafer W on the main chuck 227 with respect to a probe 226a of the probe card 226 by operating the driving element 228. An electrode pad (not shown) of the humidity sensor 100 in the wafer W disposed on the main chuck 227 and the probe 226a of the probe card 226 are aligned each other so that the electrode pad and the probe 226a are electrically connected together through the driving element 228 and the alignment element 229.

Further, the probe device 220 includes a temperature-humidity control portion 230 for controlling the humidity and the temperature of the inside of the probe portion 222.

The temperature-humidity control portion 230 supplies the gas having a predetermined temperature and a predetermined humidity, which are controlled by the temperature-humidity control portion 230, into the inside of the probe portion 222. Further, the temperature-humidity control portion 230 maintains the pressure in the probe portion 222 to be constant, or the temperature-humidity control portion 230 substitutes the gas in the probe portion 222. Specifically, on the basis of the signal from the control portion 223, the temperature-humidity control portion 230 supplies the gas adjusted to have the predetermined temperature and the predetermined humidity into the inside of the probe portion 222. The temperature-humidity control portion 230 changes the temperature and the humidity of the gas to be supplied into the probe portion 222 to have different conditions, i.e., a different temperature and a different humidity. Further, the temperature-humidity control portion 230 stops to supply the gas into the probe portion 222. Here, the temperature-humidity control portion 230 can control the temperature and the humidity of the gas by a well-known diffluence method, a well-known two-temperature method or a well-known two-pressure method.

A temperature-humidity sensing portion 231 detects the temperature and the humidity in the probe portion 222. When the temperature signal and the humidity signal outputted from the temperature-humidity sensing portion 231 satisfy a predetermined temperature-humidity condition, which is set to have a predetermined margin, i.e., to be in a predetermined range, the control portion 223 operates the driving element 228 and the alignment element 229. Here, the predetermined margin has, for example, error within 1%. The electrode pad of the humidity sensor 100 in the wafer W on the main chuck 227 and the probe 226a of the probe card 226 are aligned at a predetermined position so that the electrode pad of the humidity sensor 100 and the probe 226a electrically contact each other.

The adjustment of the sensor characteristics of the humidity sensor 100 is explained as follows. Here, the probing test and the sensor characteristic test are performed simultaneously.

Firstly, the sensitivity of the sensor 100 as one of the sensor characteristics is adjusted. In the adjustment step of the sensitivity, the temperature is kept at a constant, and the humidity is changed to different conditions. Specifically, the temperature-humidity control portion 230 roughly controls the temperature and the humidity in the probe portion 222 to be the first condition, which is, for example, the temperature of 25° C. and the humidity of 50% RH. The tester 210 detects the output of the humidity sensor 100, i.e., the tester 210 detects the sensor characteristic so that the sensor characteristic test is performed. Then, the tester 210 sends a signal to the humidity sensor 100 for controlling the output of the humidity sensor 100 to be a predetermined value, for example, to be in a range of 2.5V±1.0V when the output range is between 0V and 5V. Thus, the offset of the sensor 100 is roughly adjusted. This sensor characteristic test provides the probing test. Therefore, when the tester 210 decides the sensor to be a defective product, i.e., to have an IC failure, the test of the sensor 100 ends at this time.

Next, the temperature-humidity control portion 230 controls the temperature and the humidity in the probe portion 222 to be the second condition and the third condition sequentially. Here, the second condition is, for example, the temperature of 25° C. and the humidity of 20% RH, and the third condition is, for example, the temperature of 25° C. and the humidity of 80% RH. Under each condition, the tester 210 detects the output of the sensor 100. On the basis of the results of the sensor characteristic test under the second and the third conditions, the tester 210 calculates the sensitivity of the humidity sensor 100. Then, the tester 210 sends the signal to the humidity sensor 100 so that the sensitivity of the sensor 100 is adjusted. Specifically, for example, the adjustment data is written in an EPROM of the circuit portion 170 in the sensor 100.

Preferably, the temperature-humidity control portion 230 controls the temperature and the humidity in the probe portion 222 to be the first condition again. At this time, the output of the sensor 100 is fine adjusted to be 2.5V. Thus, the fine adjustment of the offset of the sensor 100 is performed.

Next, the temperature dependency, i.e., the temperature characteristic of the sensitivity of the sensor 100 is adjusted. In the adjustment step of the temperature characteristic, the humidity is kept at a constant, and the temperature is changed to different conditions. Specifically, the temperature-humidity control portion 230 controls the temperature and the humidity in the probe portion 222 to be the fourth condition and the fifth condition sequentially. Here, the fourth condition is, for example, the temperature of 5° C. and the humidity of 80% RH, and the fifth condition is, for example, the temperature of 45° C. and the humidity of 80% RH. Under each condition, the tester 210 detects the output of the sensor 100. On the basis of the results of the sensor characteristic test under the fourth and the fifth conditions, the tester 210 calculates the temperature characteristic of the humidity sensor 100. Then, the tester 210 sends the signal to the humidity sensor 100 so that the temperature characteristic of the sensitivity of the sensor 100 is adjusted. Specifically, for example, the adjustment data is written in the EPROM of the circuit portion 170 in the sensor 100.

Here, when the tester 210 decides the sensor to be a defective product, i.e., to have an IC failure on the basis of the sensor characteristic test under each condition, the test of the sensor 100 ends at this time. Specifically, when the sensor characteristics of the sensor 100 cannot be adjustable or be out of the adjustable range, the sensor 100 is decided as the sensor characteristic failure, i.e., the defective product.

By using the inspection device 200 for inspecting the humidity sensor 100 and by using the sensor characteristic adjustment method for adjusting the sensor 100, not only the probing test but also the sensor characteristic test are performed even when the sensor 100 is disposed in the wafer W, i.e., in the wafer state without dividing into IC chips. Here, the sensor characteristic test is the sensitivity test, the temperature characteristic test of the sensitivity, the offset test and the temperature characteristic test of the offset. On the basis of these tests, the sensor characteristics of the humidity sensor 100 are adjusted. Accordingly, the manufacturing cost of the sensor 100 is reduced.

Further, since a part of the sensor characteristic test provides the probing test, the test time, i.e., the measurement time is also reduced, so that the manufacturing cost of the sensor 100 is reduced.

In this embodiment, the sensitivity and the temperature characteristic of the sensitivity are detected and adjusted by the temperature-humidity control portion 230 under five conditions of the temperature and the humidity in the probe portion 222. Alternatively, the sensitivity may be detected and adjusted under two conditions having the same temperature and different humidity, and the temperature characteristic of the sensitivity may be detected and adjusted under two conditions having the same humidity and different temperature. Specifically, when the temperature characteristic of the sensitivity is detected and adjusted, one of two different conditions may be set to be the same condition as one of two conditions in a case where the sensitivity is detected and adjusted. In this case, the sensitivity and the temperature characteristic of the sensitivity can be adjusted by using three different conditions. Thus, the detection and adjustment time is shortened.

In this embodiment, the tester 210 adjusts the sensitivity and the temperature characteristic of the sensitivity in the sensor 100 on the basis of the sensor characteristic test. However, a characteristic adjusting device may be additionally formed in the inspection device 200. The characteristic adjusting device adjusts the sensitivity, the temperature characteristic of the sensitivity, the offset and the temperature characteristic of the offset on the basis of the sensor characteristics detected by the tester 210.

Second Embodiment

Figure 4:
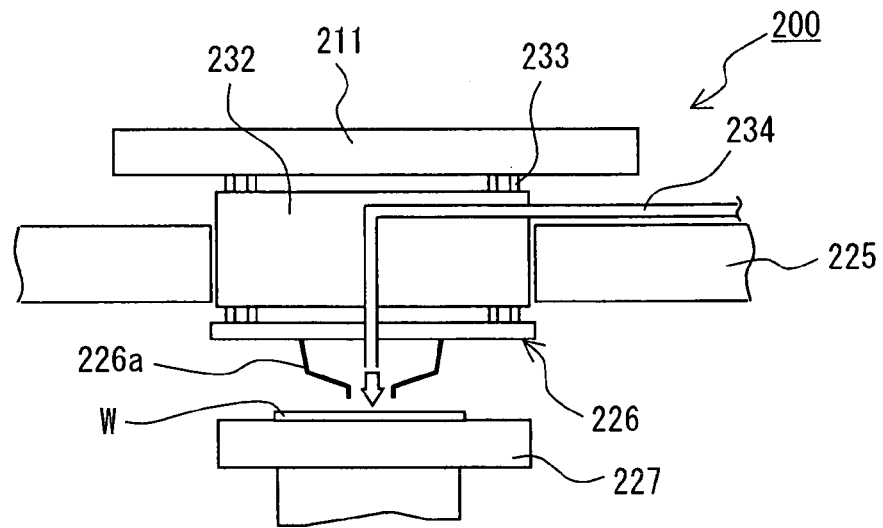
FIG. 4 is a partially enlarged schematic view showing an inspection device according to a second embodiment of the present invention.

An inspection device 200 according to a second embodiment of the present invention is shown in FIG. 4. FIG. 4 is a partially enlarged view showing the probe card 226 in the inspection device 200. The probe card 226 is fixed to a bottom side of a contact ring 232 by fixing means (not shown). The contact ring 232 and the probe card 226 are electrically connected with a spring pin 233. The contact ring 232 is also fixed to the head plate 225 with another fixing means (not shown).

The electric properties of the sensor 100 are detected and tested as follows. The tester head 211 press-contacts the top side of the contact ring 232 so that the tester head 211 and the contact ring 232 are electrically connected with the spring pin 233. Then, the main chuck 227 is elevated so that the probe 226a contacts the electrode pad of the humidity sensor 100 in the wafer W. Thus, the tester 210 inspects the electric properties of the sensor 100, i.e., the probing test. Specifically, the sensor characteristic test and the sensor characteristic adjustment are performed by the tester 210 under the above contact condition.

When the inspection device 200 includes the temperature-humidity control portion 230 according to the first embodiment, a long time is required for stabilizing the temperature and the humidity in the probe portion 222 within a predetermined margin of the temperature-humidity condition, for example, within error of ±1%. On the other hand, the inspection device 200 according to the second embodiment further includes a gas supply portion 234 for blowing the gas to the wafer W while the sensor characteristics are detected. Specifically, the gas supply portion 234 blows the gas having a predetermined temperature and a predetermined humidity, which is the same condition as the temperature and the humidity in the probe portion 222 to be set. FIG. 4 shows a part of the gas supply portion 234, and the gas supply portion 234 is disposed through the contact ring 232 and the probe card 226 so that the gas supply portion 234 blows the gas to the wafer W.

Accordingly, since the gas having the predetermined temperature and the predetermined humidity is directly blown to the wafer W, even when the temperature and the humidity in the probe portion 222 is in a wider margin, which is wider than a predetermined margin, and has, for example, error within 3%, the sensor characteristics are detected accurately. Thus, the waiting time for starting the test of the sensor characteristics is reduced.

The gas supply portion 234 may have another construction other than the portion shown in FIG. 4 as long as the gas supply portion 234 is capable of blowing the gas having a predetermined temperature and a predetermined humidity.

(Modifications)

The inspection device 200 may have another construction other than the device shown in FIGS. 3 and 4 as long as the device 200 measures electric properties of the humidity sensor 100 in the wafer state before the wafer W is divided into IC chips under multiple conditions having different temperature and different humidity of environment around the humidity sensor 100. Further, the humidity sensor 100 includes the sensor portion 160 and the circuit portion 170, which are integrated into one chip. Preferably, the inspection device 200 adjusts the sensor characteristics of the sensor 100 on the basis of the measurement results of the electric properties, the sensor characteristics which are the sensitivity, the temperature characteristics of the sensitivity, the offset and the temperature characteristics of the offset.

Figure 5:
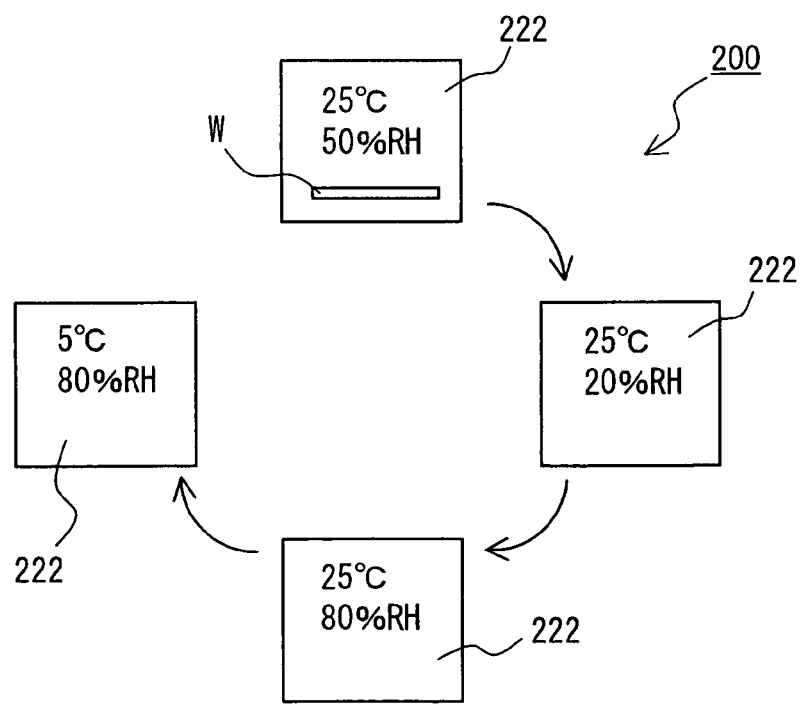
FIG. 5 is a schematic diagram explaining an inspection device according to a modification of the first and second embodiments of the present invention.

Although the inspection device 200 includes one probe portion 222 as an inspection chamber for inspecting the wafer W, the inspection device 200 may have multiple probe portions 222, as shown in FIG. 5. In FIG. 5, each probe portion 222 has different temperature and different humidity, respectively. The inspection device 200 includes four probe portions 222 in FIG. 5. In this case, the wafer W is transported from the first probe portion 222 to the fourth probe portion 222. Thus, the sensor characteristics are detected and adjusted, so that the manufacturing cost of the sensor 100 is reduced. Further, multiple probe portions 222 are preliminarily controlled to be a predetermined temperature and a predetermined humidity independently. Thus, the waiting time for starting the test is shortened. Accordingly, many sensors 100 can be tested within short time.

Although the humidity sensor 100 has the comb-shape electrodes 131, 132, the humidity sensor 100 may have another construction as long as the sensor 100 includes the sensor portion 160 for detecting the humidity and the circuit portion 170 for processing the detected signal from the sensor portion 160, and the sensor portion 160 and the circuit portion 170 are integrated into one chip and are electrically connected together. Here, in the humidity sensor 100 according to this embodiment, the sensor portion 160 and the circuit portion 170 may be easily integrated into one chip.

The present invention provides following example aspects.

An inspection device inspects a humidity sensor having a sensor portion and a circuit portion, which are integrated into one chip. The sensor portion is capable of detecting humidity of atmosphere, and the circuit portion is electrically connected to the sensor portion so that the circuit portion is capable of processing a detection signal of the sensor portion. The inspection device includes: an inspection chamber for accommodating a wafer, the wafer in which a plurality of humidity sensors are disposed as a sensor chip in a wafer state; a probe as a contact member for contacting an electrode pad of the circuit portion, wherein the probe is disposed in the inspection chamber; a tester for inspecting electric properties of the humidity sensor in the wafer state, wherein the tester is electrically connected to the probe for inspecting the humidity sensor; and a temperature-humidity control portion for controlling a temperature and a humidity in the inspection chamber.

In the above inspection device, since the temperature-humidity control portion controls a temperature and a humidity in the inspection chamber to be a predetermined temperature-humidity condition, not only the probing test but also the sensor characteristic test are performed by the tester. Thus, the manufacturing cost of the humidity sensor is reduced. Further, by performing the sensor characteristic test and the probing test simultaneously, the manufacturing cost of the humidity sensor is much reduced.

Alternatively, the temperature-humidity control portion may be capable of supplying a gas into the inspection chamber, the gas having a predetermined temperature and a predetermined humidity, and the temperature-humidity control portion may substitute the gas for air in the inspection chamber. Alternatively, the device may further includes: a gas supply portion for blowing a gas having a predetermined temperature and a predetermined humidity to the wafer in the inspection chamber while the electric properties of the humidity sensor are inspected by the tester. Alternatively, the device may further includes: a sensor characteristic control portion for adjusting a sensitivity, a temperature characteristic of the sensitivity, an offset and a temperature characteristic of the offset in the humidity sensor on the basis of an inspection result of the electric properties of the humidity sensor. Further, the sensor characteristic control portion is provided by the tester.

Alternatively, the temperature-humidity control portion may be capable of controlling pressure in the inspection chamber to be constant while the electric properties of the humidity sensor are inspected by the tester.

Further, an inspection device inspects a humidity sensor having a sensor portion and a circuit portion, which are integrated into one chip. The sensor portion is capable of detecting humidity of atmosphere, and the circuit portion is electrically connected to the sensor portion so that the circuit portion is capable of processing a detection signal of the sensor portion. The inspection device includes: a plurality of inspection chambers for accommodating a wafer, the wafer in which a plurality of humidity sensors are disposed as a sensor chip in a wafer state; a probe as a contact member for contacting an electrode pad of the circuit portion, wherein the probe is disposed in the inspection chamber; and a tester for inspecting electric properties of the humidity sensor in the wafer state, wherein the tester is electrically connected to the probe for inspecting the humidity sensor. Each inspection chamber has a different temperature and a different humidity, and the wafer is transported from one inspection chamber to another in turn so that the tester inspects the humidity sensor in the wafer state under different temperature-humidity conditions.

In the above inspection device, the wafer is transported from one inspection chamber to another. Thus, the sensor characteristics of the humidity sensor are inspected effectively. Thus, the manufacturing cost of the humidity sensor is reduced. Further, since each inspection chamber is preliminarily controlled to have a predetermined temperature and a predetermined humidity, the waiting time for starting the test is shortened. Accordingly, many humidity sensors can be inspected within short time.

Further, a method for adjusting sensor characteristics of a humidity sensor is provided. The humidity sensor has a sensor portion and a circuit portion, which are integrated into one chip. The sensor portion is capable of detecting humidity of atmosphere, and the circuit portion is electrically connected to the sensor portion so that the circuit portion is capable of processing a detection signal of the sensor portion. The method includes the steps of: controlling a temperature and a humidity around a wafer to be a predetermined temperature-humidity condition, the wafer in which a plurality of humidity sensors are disposed as a sensor chip in a wafer state before the wafer is divided into a plurality of sensor chips; measuring electric properties of the humidity sensor under the predetermined temperature-humidity condition; and adjusting a sensitivity, a temperature characteristic of the sensitivity, an offset and a temperature characteristic of the offset in the humidity sensor on the basis of a measurement result of the electric properties of the humidity sensor.

In the above method, not only the probing test but also the sensor characteristic test are performed even when the humidity sensor is in the wafer state, i.e., even when the wafer is not divided into multiple sensor chip. Further, on the basis of the test result, the sensor characteristics of the humidity sensor are adjusted. Thus, the manufacturing cost of the humidity sensor is reduced.

Alternatively, the step of controlling the temperature and the humidity around the wafer and the step of measuring the electric properties of the humidity sensor may be performed by a plurality of times under different temperature-humidity conditions so that the sensitivity, the temperature characteristic of the sensitivity, the offset and the temperature characteristic of the offset in the humidity sensor are adjusted in the step of adjusting. Further, the different temperature-humidity conditions may include two conditions having a same temperature and a different humidity and two conditions having a same humidity and a different temperature. Alternatively, the step of measuring the electric properties of the humidity sensor may include a probing test of the humidity sensor in the wafer state.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. An inspection device for inspecting a humidity sensor having a sensor portion and a circuit portion, which are integrated into one chip, wherein the sensor portion is capable of detecting humidity of atmosphere, and wherein the circuit portion is electrically connected to the sensor portion so that the circuit portion is capable of processing a detection signal of the sensor portion, the inspection device comprising:
   an inspection chamber for accommodating a wafer, the wafer in which a plurality of humidity sensors are disposed as sensor chips in a wafer state;
   a probe as a contact member for contacting an electrode pad of the circuit portion, wherein the probe is disposed in the inspection chamber;
   a tester for inspecting electric properties of at least one of the humidity sensors in the wafer state, wherein the tester is electrically connected to the probe for inspecting the at least one humidity sensor; and
   a temperature-humidity control portion for controlling a temperature and a humidity in the inspection chamber.

2. The device according to claim 1, wherein the temperature-humidity control portion is capable of supplying a gas into the inspection chamber, the gas having a predetermined temperature and a predetermined humidity, and the temperature-humidity control portion substitutes the gas for air in the inspection chamber.

3. The device according to claim 1, wherein
   the sensor portion of the humidity sensors includes a substrate, a pair of comb-shape electrodes and a humidity sensitive film,
   the comb-shape electrodes are disposed on the substrate, face each other, are separated from each other, and are interleaved with each other,
   the humidity sensitive film covers the comb-shape electrodes and a clearance between the comb-shape electrodes, the comb-shape electrodes provide a capacitor having a capacitance between the comb-shape electrodes, and
   the capacitance is changeable in accordance with the humidity of the atmosphere.

4. The device according to claim 1, wherein the temperature-humidity control portion is capable of controlling pressure in the inspection chamber to be constant while the electric properties of the at least one humidity sensor are inspected by the tester.

5. An inspection device for inspecting a humidity sensor having a sensor portion and a circuit portion, which are integrated into one chip, wherein the sensor portion is capable of detecting humidity of atmosphere, and wherein the circuit portion is electrically connected to the sensor portion so that the circuit portion is capable of processing a detection signal of the sensor portion, the inspection device comprising:
   a plurality of inspection chambers for accommodating a wafer, on which a plurality of humidity sensors are disposed as sensor chips in a wafer state;
   a plurality of probes, which serve as contact members, for contacting an electrode pad of the circuit portion, wherein each probe is located in a corresponding one of the inspection chambers; and
   a tester for inspecting electric properties of at least one of the humidity sensors in the wafer state, wherein the tester is electrically connected to the probes for inspecting the at least one humidity sensor, wherein each inspection chamber has a different temperature and a different humidity, and the wafer is transported from one inspection chamber to another in turn so that the tester inspects the at least one humidity sensor in the wafer state under different temperature-humidity conditions.

6. The device according to claim 5, wherein the sensor portion of the humidity sensors includes a substrate, a pair of comb-shape electrodes and a humidity sensitive film, the comb-shape electrodes are disposed on the substrate, face each other, are separated from each other, and are interleaved with each other, the humidity sensitive film covers the comb-shape electrodes and a clearance between the comb-shape electrodes, the comb-shape electrodes provide a capacitor having a capacitance between the comb-shape electrodes, and the capacitance is changeable in accordance with the humidity of the atmosphere.

7. The device according to claim 5, wherein the temperature-humidity control portion is capable of controlling pressure in the inspection chamber to be constant while the electric properties of the at least one humidity sensor are inspected by the tester.

* * * * *